(12) United States Patent
Nguyen et al.

(10) Patent No.: US 7,449,698 B2
(45) Date of Patent: Nov. 11, 2008

(54) METHOD FOR ENCODING MATERIALS WITH A LUMINESCENT TAG AND APPARATUS FOR READING SAME

(75) Inventors: Brian D. Nguyen, Kirkland (CA); Duc-Huy Giang, Laval (CA); My T. Nguyen, Kirkland (CA)

(73) Assignee: American Dye Source, Inc., Baie d'Urfé (CA)

( * ) Notice: Subject to any disclaimer, the term of this patent is extended or adjusted under 35 U.S.C. 154(b) by 0 days.

(21) Appl. No.: 11/356,011

(22) Filed: Feb. 17, 2006

(65) Prior Publication Data

US 2006/0186348 A1    Aug. 24, 2006

Related U.S. Application Data

(60) Provisional application No. 60/653,980, filed on Feb. 18, 2005.

(51) Int. Cl.
*H05B 33/00* (2006.01)
(52) U.S. Cl. ............... 250/484.4; 250/459.1; 250/483.1
(58) Field of Classification Search .............. 250/484.4, 250/483.1, 459.1; 436/171; 435/6; 356/244
See application file for complete search history.

(56) References Cited

U.S. PATENT DOCUMENTS

| | | | | |
|---|---|---|---|---|
| 3,801,782 | A | | 4/1974 | Dorlon |
| 5,573,909 | A | * | 11/1996 | Singer et al. .................... 435/6 |
| 5,918,960 | A | | 7/1999 | Hopwood et al. |
| 6,469,785 | B1 | * | 10/2002 | Duveneck et al. ........... 356/244 |
| 6,612,494 | B1 | * | 9/2003 | Outwater ............... 235/462.04 |
| 2002/0022273 | A1 | * | 2/2002 | Empedocles et al. ........ 436/171 |
| 2002/0158212 | A1 | * | 10/2002 | French et al. ............ 250/459.1 |
| 2003/0002029 | A1 | | 1/2003 | Dukler et al. |
| 2003/0141375 | A1 | * | 7/2003 | Lawandy ..................... 235/494 |

FOREIGN PATENT DOCUMENTS

| | | |
|---|---|---|
| CA | 2449171 | 12/2002 |
| EP | 0 342 772 A2 | 11/1989 |
| EP | 1 151 870 A1 | 11/2001 |
| EP | 1 179 808 A1 | 2/2002 |
| FR | 2813134 A | 2/2002 |
| JP | 2005-246821 A | 9/2005 |
| WO | WO 98/22291 | 5/1998 |
| WO | WO-02/46528 A | 6/2002 |

\* cited by examiner

*Primary Examiner*—David P. Porta
*Assistant Examiner*—Jessica L Eley
(74) *Attorney, Agent, or Firm*—Goudreau Gage Dubuc

(57) ABSTRACT

A method, apparatus and system for analysing and authenticating a luminescent tag are provided wherein a luminescence is triggered in the tag and relative light intensities emitted thereby measured within at least two luminescence bands. The measured intensities are compared with at least one reference tag representative of relative intensities emitted by an authentic tag to determine whether the luminescent tag corresponds with any of the at least one reference tag. If the measured intensities match the representative intensities, the luminescent tag is authenticated. A computer program to be implemented by the apparatus and system is also disclosed. Further, a method and system for verifying the authenticity of one or plural objects are disclosed, wherein each of the objects is to be associated with a respective tag. The respective tags are coded to emit light, when triggered, within at least two luminescence bands at respective predetermined relative light intensities. Having access to a reference tag representative of the predetermined intensities, the authenticity of a luminescent tag is verified by measuring intensities emitted thereby within the luminescence bands and comparing the measured intensities with the predetermined intensities.

40 Claims, 8 Drawing Sheets

METHOD FOR ENCODING MATERIALS WITH A LUMINESCENT TAG AND APPARATUS FOR READING SAME

CROSS REFERENCE TO RELATED APPLICATIONS

This application claims priority on U.S. Provisional Application No. 60/653,980, filed on Feb. 18, 2005, the entire contents of which is herein incorporated by reference.

FIELD OF THE INVENTION

The invention relates to a method for encoding materials with a luminescent tag and an apparatus for reading same. The invention also relates to a method and system for verifying the authenticity of an object.

BACKGROUND OF THE INVENTION

Materials which fluoresce when exposed to UV light are well known in the art. Such fluorescent materials absorb UV radiation of one wavelength and emit UV or thermal radiation at a longer wavelength. Fluorescent materials are finding many uses in the fight against counterfeiting by providing a means for imprinting or tagging objects or materials in a manner which is only visible when illuminated by UV light.

Also known in the art is the effect of Fluorescence Resonance Energy Transfer (FRET) where UV light is absorbed by a first fluorescing material which emits radiation at a wavelength within the absorption spectrum of a second fluorescing material. Depending on the type of fluorescing materials all or a portion of the radiation emitted by the first fluorescing material is absorbed by the second fluorescing material, which in turn emits radiation at a third longer wavelength.

Prior art documents which discuss various aspects of such materials and their use are U.S. Pat. No. 3,801,782 by Dorion, the international application published with the number WO 98/22291 by Cyr, et al., and Canadian Patent Application No. 2,449,171 by Smuk, et al. the entire contents of which are incorporated herein by reference.

SUMMARY OF THE INVENTION

In order to address the above and other drawbacks of known techniques, there is provided, in accordance with the present invention, a method for authenticating a luminescent tag, the method comprising the steps of providing a reference tag representative of relative light intensities emitted within two luminescence bands; triggering the luminescent tag; measuring, within the two luminescence bands, light intensities emitted from the triggered tag; and comparing the measured intensities with the representative intensities. If the measured intensities match the representative intensities, the luminescent tag is authenticated.

Also in accordance with the present invention, there is provided a method for verifying the authenticity of an object, the method comprising the steps of: associating a luminescent tag with the object; coding the luminescent tag by adjusting relative light intensities emitted thereby within at least two luminescence bands; and authenticating the object by triggering the luminescent tag, measuring a light spectrum emitted thereby and comparing the measured spectrum with a reference spectrum. If the measured spectrum matches the reference spectrum, the object is authenticated.

Further in accordance with the present invention, there is provided a system for verifying the authenticity of an object, the system comprising a luminescent tag to be associated with the object, the luminescent tag coded to emit light when triggered within at least two luminescence bands at predetermined relative light intensities; a reference tag representative of the predetermined intensities; and a monitoring station having access to the reference tag, the station comprising a spectrometer, a data processor and an output device and being configured to measure light intensities emitted within the luminescence bands by the coded tag via the spectrometer, compare the measured intensities with the predetermined intensities and indicate via the output device whether the measured intensities match the predetermined intensities.

Still further in accordance with the present invention, there is provided a use of such a system for anti-counterfeiting.

Still further in accordance with the present invention, there is provided an apparatus for authenticating a luminescent tag, the apparatus comprising a reference tag representative of relative light intensities emitted within at least two luminescence bands; a spectrometer for measuring light intensities emitted from the luminescent tag within the luminescence bands; a data processor configured to compare the measured intensities with the representative intensities; and an output device for indicating whether the measured intensities match the representative intensities. If the measured intensities match the representative intensities, the object is authenticated.

Still further in accordance with the present invention, there is provided a computer-readable storage medium having a computer-readable program embodied therein for directing operations of a computer system comprising a spectrometer, a data processor, a storage device and an output device, wherein the computer-readable program comprises instructions for operating the computer system to authenticate a luminescent tag associated with an object in accordance with the following: storing in the storage device a reference tag representative of relative light intensities emitted within at least two luminescence bands; measuring, via the spectrometer, light intensities emitted from the luminescent tag within the luminescence bands; using the processor, comparing the measured intensities with the representative intensities; and indicating, via the output device, whether the measured intensities match the representative intensities. If the measured intensities match the representative intensities, the object is authenticated.

Still further in accordance with the present invention, there is provided a method for incorporating a luminescent code into a material comprising the steps of: combining a donor luminescent substance with an acceptor luminescent substance, wherein an emission spectrum of the donor substance overlaps with an absorption spectrum of the acceptor substance; irradiating the combined substances with a high power source of ultraviolet radiation, the radiation comprising a wavelength which lies within an absorption spectrum of the donor substance; adjusting an energy of the radiation such that when the combined substances are subsequently irradiated with a low power source of ultraviolet radiation, an intensity of measurable emissions of the donor substance versus an intensity of peak measurable emissions of the acceptor substance is of a predetermined ratio; and combining the combined substances with the material.

Other objects, advantages and features of the present invention will become more apparent upon reading of the following non-restrictive description of illustrative embodiments thereof, given by way of example only with reference to the accompanying drawings.

DETAILED DESCRIPTION OF THE ILLUSTRATIVE EMBODIMENTS

Figure 1:
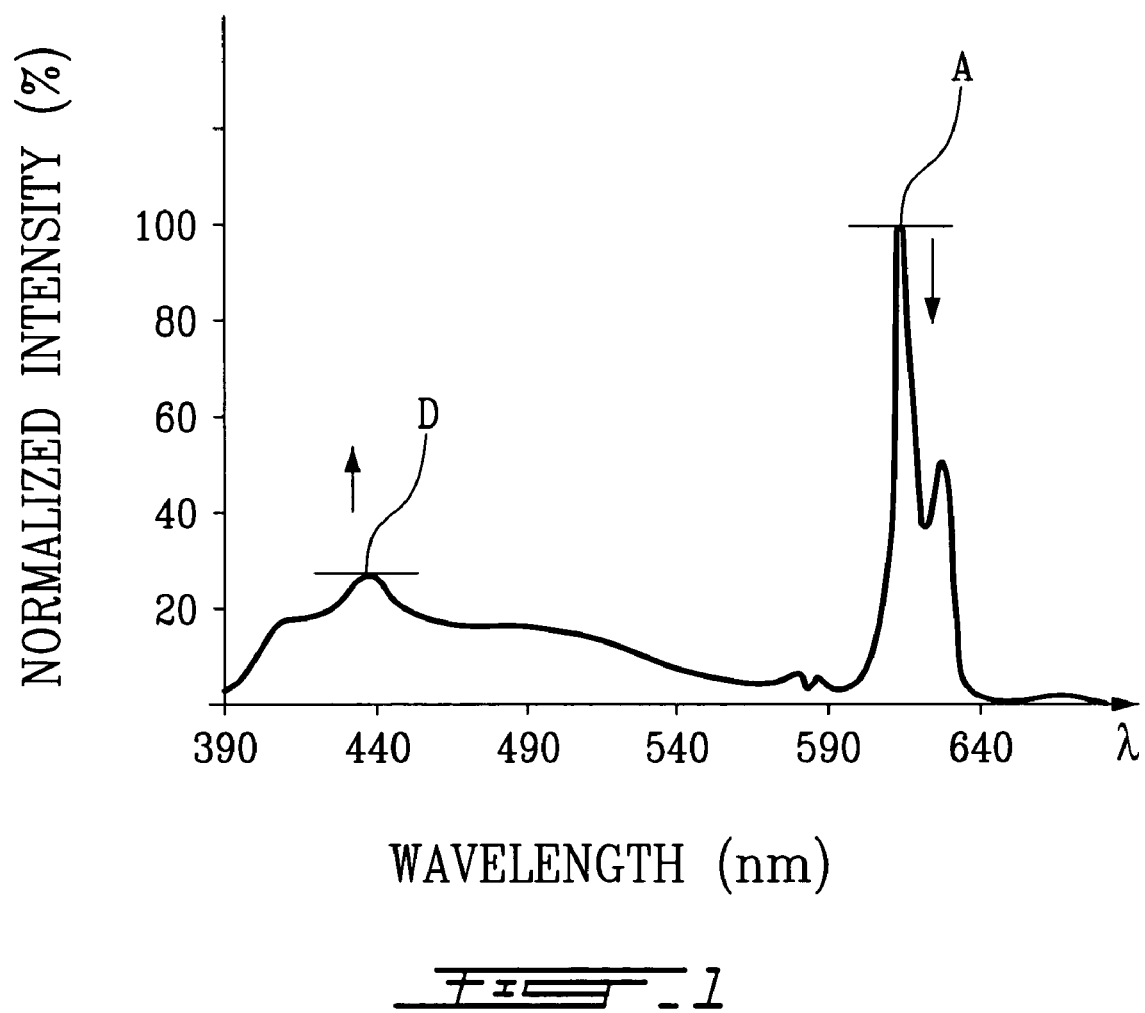
FIG. 1 shows the luminescence spectrum of a mixed luminescent composition.

In general terms, the present invention partially relates to a method for recording a luminescent tag into or onto an object for applications such as security printing, anti-counterfeiting, automatic identification, chemical sensors, bio-sensors, laser marking, laser imaging and display devices. The luminescent compositions used in the present invention are comprised of a combination of two or more materials which each fluoresce, phosphoresce or emit infrared (IR) radiation of a particular wavelength, or within a particular luminescence band, when triggered by light waves of a different wavelength or by an applied electric current.

The luminescent compositions used in the illustrative embodiments presented hereinbelow are irradiated with a photon source of a given power to provide luminescent compositions which emit radiation at multiple wavelengths and predefined relative intensities via fluorescent, phosphorescent and/or IR emissions upon exposure to radiation having a shorter wavelength than the luminescent wavelength.

As used herein, the term "luminescent" refers to a material or composition being capable of emitting light by exposure to light waves, such as low intensity UV radiation (photoluminescence) and under applied electric current (electroluminescence). The term "luminescent" also encompasses herein fluorescent, phosphorescent and IR radiation.

In general terms, an exemplary method for recording a luminescent tag onto or into a material in accordance with the illustrative embodiments of the present invention, may comprise the following basic steps of:

a) providing a luminescent composition comprising at least two luminescent compounds in a suitable carrier or diluent;

b) combining the luminescent composition with a substrate, so that at least a portion of the composition is available for exposure to a photon source; and c) adjusting the relative emission intensities of the at least two luminescent compounds by exposure to a photon source;

the step of adjusting the relative emission intensities resulting in a characteristic tag comprised of light of varying wavelengths and relative intensities being emitted when the substrate is subsequently exposed to, as the case may be, a source of low intensity UV radiation or electric current. In one exemplary embodiment, the step of adjusting the relative emission intensities may be implemented to provide a characteristic tag whose relative emission light intensities correspond with a predefined reference light spectrum or tag to be used for tag authentication purposes. Alternatively, the characteristic tag generated through the adjusting step may be used to define such a reference spectrum or tag. Other techniques for selecting and defining such reference spectra and/or tags will become apparent to the person of skill in the art upon reference to the following description of illustrative embodiments.

In the above exemplary method, the luminescent compositions used generally comprise at least a first and second luminescent compound, wherein the first luminescent compound is a donor compound having a peak luminescent emission spectrum/band at a given wavelength, wherein the second luminescent compound is an acceptor compound having a peak absorption spectrum/band at a longer wavelength than the given wavelength, and wherein the emission spectrum/band of the donor compound at least partially overlaps the absorption spectrum/band of the acceptor compound.

More specifically, the luminescent compounds contained in the compositions used in the above method may include organic materials and organic metal complexes. The organic materials may contain conjugated or non-conjugated backbones and may exhibit peak luminescent properties when exposed to radiation of typically between ?=370 and ?=1100 nm.

Before exposure to a photon source for adjusting the relative emission intensities, a luminescent composition used in the above method is combined with a substrate, in such a way that at least a portion of the composition is available for exposure to the photon source. Examples of various possible substrates are plastics, papers, metal films, wood, glass and ceramic surfaces, devices such as flexible displays or any other article of manufacture.

Combining a luminescent composition with a substrate may be achieved, for example, by conventional coating, spraying, jetting and similar techniques. Combining can also be achieved by melt mixing, solvent casting, hot melt casting, extrusion, laminating techniques and the like into the bulk of any polymeric article. In this case, polymeric binder resins may not be needed.

When combining consists in layering the composition onto a film for example, an additional step of laminating may occur onto a secondary substrate, before or after exposure to the photon source. Such secondary substrate may be plastic, cardboard, paper, metal film, glass, ceramic surface or any other article of manufacture.

As stated above, the luminescent compositions used in the above method comprise at least a first and second luminescent compounds, wherein the first luminescent compound is a donor compound having a peak luminescent emission spectrum/band at a given wavelength, the second luminescent compound is an acceptor compound having a peak absorption spectrum/band at a longer wavelength than the given wavelength, and the emission spectrum/band of the donor compound at least partially overlaps the absorption spectrum/band of the acceptor compound.

The following illustrative embodiments of the present invention are partly based on the general principle of FRET between two luminescent compounds, an acceptor compound and a donor compound. Referring to FIG. 1, as discussed above, FRET arises, for example, when such an acceptor compound and a donor compound are mixed and submitted to UV light: the donor compound has a peak luminescent emission spectrum/band (D on FIG. 1) at a shorter wavelength than the peak absorption spectrum/band of the acceptor compound (A on FIG. 1) and the emission energy of the donor compound is absorbed by the acceptor compound. The energy transfer occurs causing the acceptor compound to emit brighter fluorescence at its proper wavelength(s) (corresponding to a given colour of the composition).

Surprisingly, it has been found that upon exposure to an increasing imaging energy density, the behaviour of the acceptor compound and the donor compound as described above in the composition, as observed under UV light, varies. Indeed, as the imaging energy density increases, the very bright colour of the acceptor compound, observed under UV light, progressively decreases in favour of the colour of the donor compound. In fact, the FRET effect is possibly gradually "replaced" by modification of the acceptor compound, the modification progressively reducing the amount of energy of the acceptor compound is able to accept from the donor compound. This results in the restoration of the luminescence of the donor compound and as a result, the ratio of the intensity of the peak luminescence D of the donor compound versus the peak luminescence A of the acceptor compound is increased.

Figure 2:
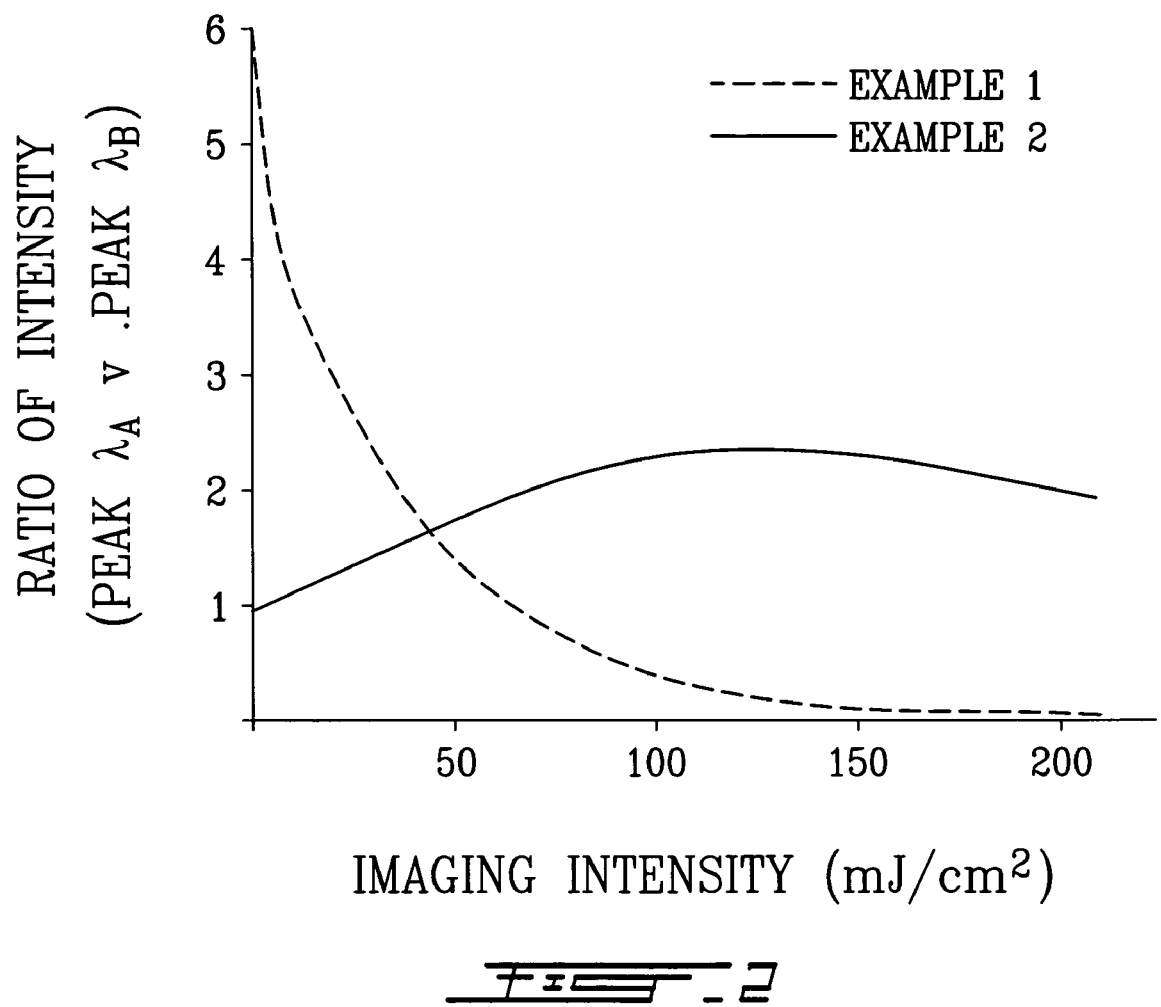
FIG. 2 shows the variation of the relative luminescent intensities of a donor compound and an acceptor compound in two exemplary mixed luminescent compositions.

Referring now to FIG. 2, the relative intensities of the emitted wavelength of a donor compound $?_D$ and an acceptor compound $?_A$ are graphed for the two examples which are discussed herein below in more detail. As will be apparent from FIG. 2, the ratio of the intensity of $?_A$ versus $?_D$ in Example 1 varies uniquely as the imaging energy density increases. Similarly, the ratio of the intensity of $?_A$ versus $?_D$ in Example 2 also varies uniquely as the imaging energy density increases up until about 100 mJ/cm$^2$.

It is in part the above effect which is used to advantage in the illustrative embodiments of the present invention. Indeed, it will now be apparent to a person of ordinary skill in the art that by subjecting a mix of a donor compound and acceptor compound to a predetermined imaging energy density, the relative intensities of the emitted wavelengths of light when observed under UV light may also be predetermined. In this regard, an object impregnated, imprinted or otherwise tagged with a mix of a donor compound and acceptor compound may be analysed not only to determine the wavelengths of light emitted, but also b determine the relative intensities of those emitted wavelengths. As a result, the relative intensities of emitted wavelengths provide another dimension which can be used for tagging and subsequently identifying objects marked in a manner which is visible only under UV light.

It is to be understood that several parameters can be varied in order to obtain various intensities of emitted wavelengths. The nature, number, and concentration of the luminescent materials in the compositions, as well as the intensity of the photon source indeed may all play a role in the resulting composition.

Illustratively, energy densities of the photon sources used in the above exemplary method may vary between 20 and 200 mJ/cm$^2$ for a laser light, preferably between 50 and 200 mJ/cm$^2$, and between 200 and 900 mJ/cm$^2$ for a UV light.

Upon exposure to a photon source for recording a luminescent tag into or onto an object, the fluorescence and phosphorescence of the compositions change in intensity or emission wavelength without significantly changing their absorption characteristics. Therefore, it is also to be understood that the recorded luminescent tag can remain essentially invisible under ambient light and that an additional reading step allows extracting the encoded tag. The recorded luminescent tag becomes discernable when exposed to, for example, black lamps, low intensity UV radiation, laser light, CCD cameras or under applied electric field.

As a general rule, the wavelengths seen with a tag reading apparatus, prior to or without exposure to a photon source, are those of the acceptor compound, and the wavelengths seen after exposure to the photon source are a combination of those of the acceptor compound and donor compound.

Moreover, the compositions used in the following illustrative embodiments of the present invention may comprise more than two luminescent compounds, which gives multiple peak intensity ratio possibilities.

The energy density required for reading materials encoded with tags according to the illustrative embodiments of the present invention is usually below 1 mJ/cm$^2$.

There are many possible uses of the tag-encoded compositions as obtained by the above method. Non-limiting examples of such uses are security printing, anti-counterfeiting, automatic identification, chemical sensors, bio-sensors and laser marking.

Many articles of manufacture may comprise tags obtained according to the above method, such as but not limited to credit card like articles and tear tape for packaging purposes.

Figure 3:
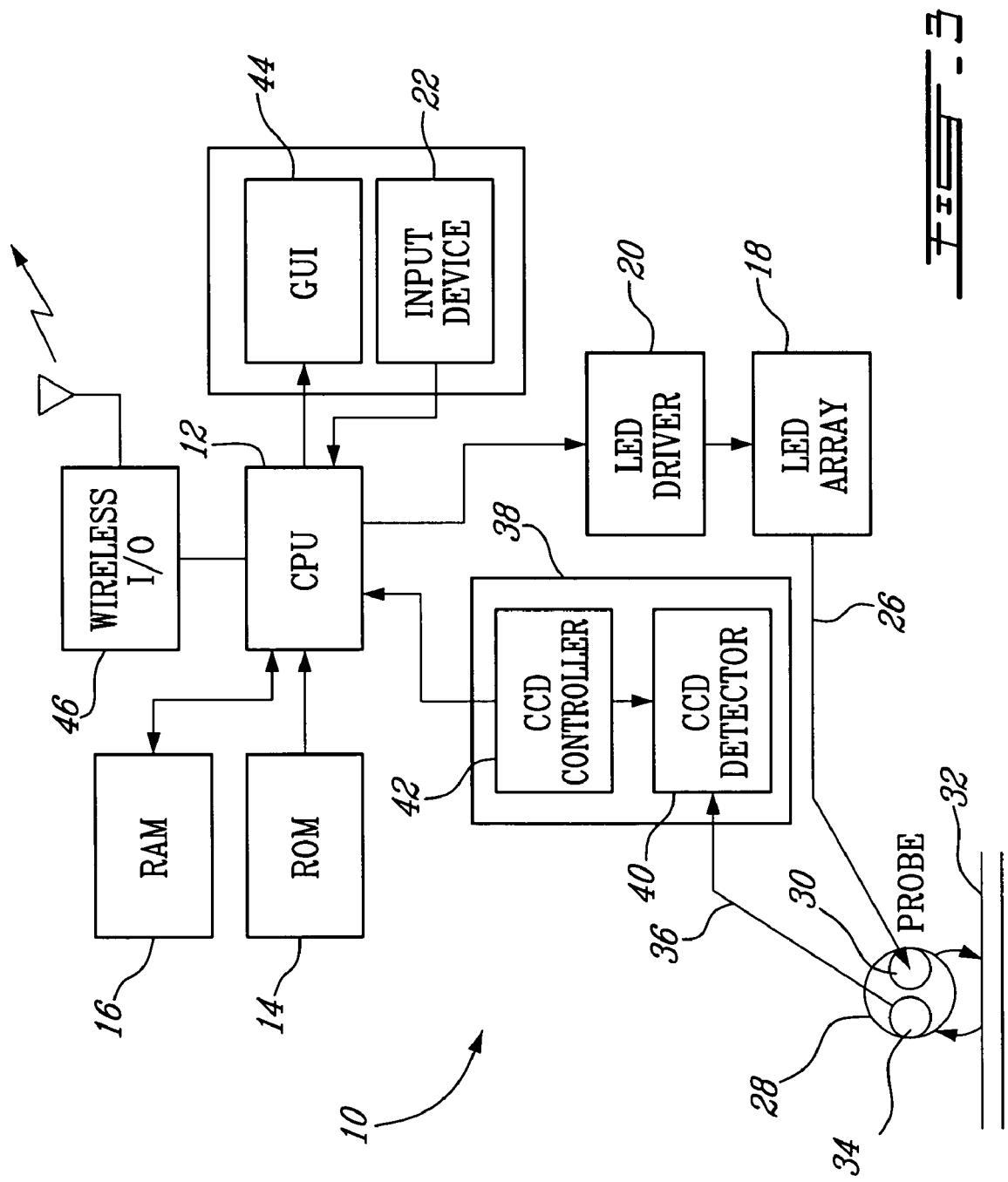
FIG. 3 shows a block diagram of a system for reading FRET encoded tags in accordance with an illustrative embodiment of the present invention.

Referring now to FIG. 3, an apparatus for reading materials encoded with a luminescent tag, generally referred to using the reference numeral 10, in accordance with an illustrative embodiment of the present invention will now be described. The apparatus 10 is comprised of a data processor or central processing unit (CPU) 12 which, using software (not shown) stored in a ROM 14, RAM 16 and/or other such media storage device(s), controls an LED Array 18 via a series of LED Drivers 20, in part based on user input received from an Input Device 22.

The individual LEDs (not shown) of the LED Array 18 emit light having predefined wavelengths. The light is transferred from the LED Array 18 via a transmitting optic fibre (or fibres) 26 to a probe 28 where it exits the end 30 of the transmitting optic fibre 26. Light emitted (photon source) from the end 30 of the transmitting optic fibre 26 is incident on a surface 32 coated or impregnated with a material which fluoresces at predetermined wavelengths within respective luminescence bands (i.e. according to a predetermined emission spectrum) when excited with light of particular wavelength.

Light emitted by the surface 32 in response to being stimulated by light emitted from the end 30 of the transmitting optic fibre 26 is collected at the end 34 of a receiving optic fibre (or fibres) 36 held in proximity to the end 30 of the transmitting optic fibre 26 and relayed to a spectrometer 38, comprised of a Charged Coupled Device (CCD) Detector 40 or the like which converts the collected light to electrical signals which are relayed to a CCD controller 42. These signals are then processed by the CPU 12 according to one or more programs stored in ROM 14 and/or RAM 16, for example for display to the user in real time on a Graphical User Interface (GUI) 44 or other such output device.

The apparatus 10 further comprises a wireless interface 46 (or other such wireless and/or wireline communication device) for communicating with external devices, via a selected wireless and/or wireline communication network, in order to download, for example, software patches and reference wavelength/amplitude tags or spectra which are then stored in RAM 16 or used to reprogram the ROM 14. Such a communication device 46 may also be used, as will be discussed further hereinbelow with reference to FIG. 10, to upload results and/or communicate warnings/flags to a central or remote monitoring station when objects scanned or read by the apparatus 10 do not correspond with any of the reference tags or spectra stored in the device 10. Additionally, in particular applications a Global Positioning System (GPS) receiver 48 could be provided to provide accurate location data to the CPU, namely to identify a location from which warnings/flags are being sent to flag unauthenticated materials or objects.

Figure 4:
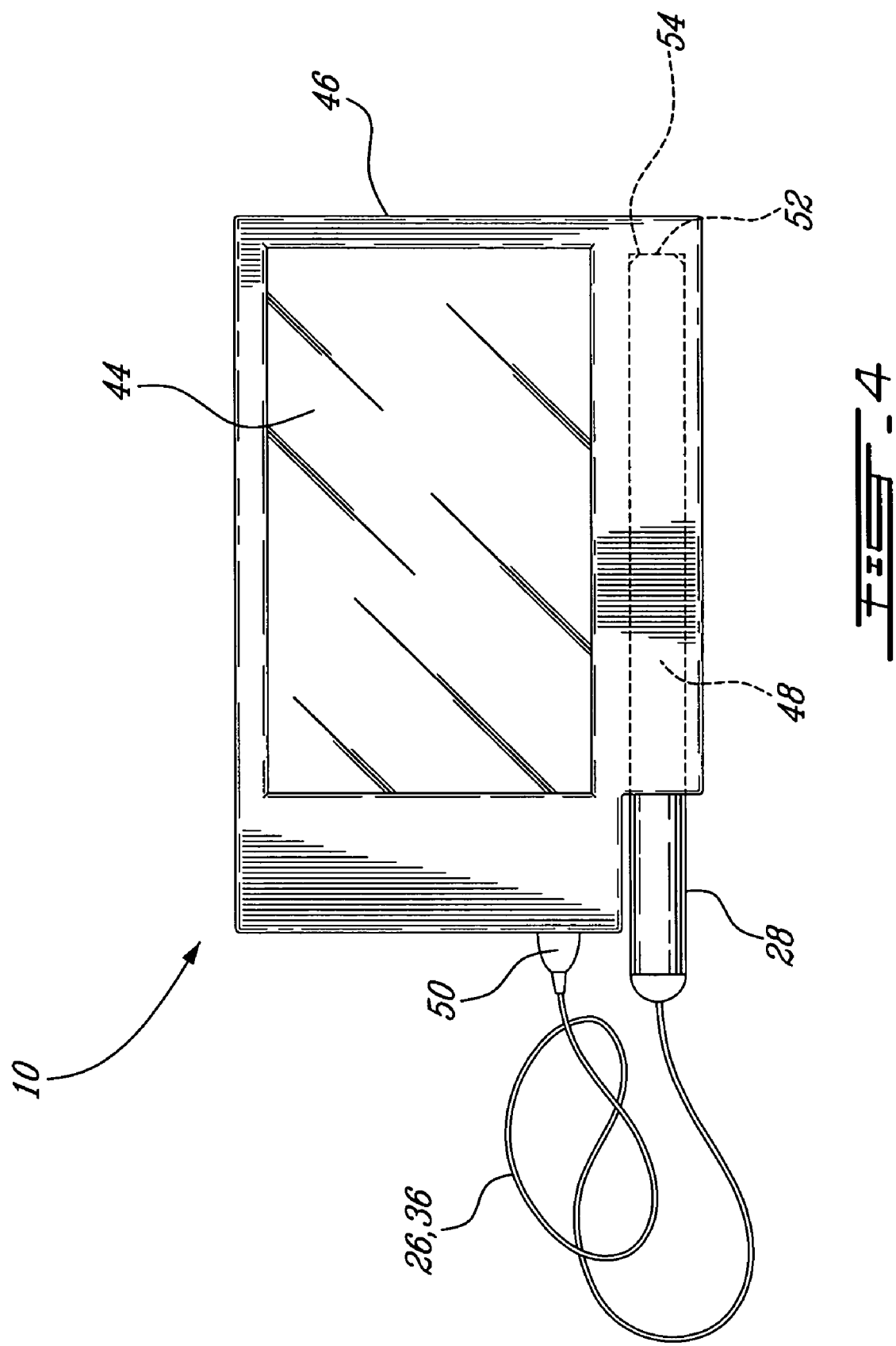
FIG. 4 shows a top plan view of an apparatus for reading FRET encoded tags in accordance with the illustrative embodiment of FIG. 3.

Referring to FIG. 4, the apparatus 10 is illustratively in the form of a handheld device similar to a PDA, and including as discussed hereinabove a GUI 44 which is mounted within a robust housing 50 manufactured from plastic, magnesium or the like. A probe sheath 52 is moulded into the housing 50, thereby providing a handy location for storing the probe 28 when it is not in use. Bundled optic fibres 26, 36 interconnect the probe 28 with an appropriate connecter 54 mounted on the side of the housing 50.

In order to calibrate the probe 28, a suitably reflective material 56 is mounted at a closed end 58 of the probe sheath 52.

Referring back to FIG. 3, in operation the probe 28 is retracted from the sheath 48 and held against a material 32 within which it is believed that a luminescent tag has been encoded. By illuminating the material with the LEDs of the array 18, the material 32 can be made to fluoresce, which fluorescence is transferred to the spectrometer 38. The CCD detector portion 40 of the spectrometer 38 collects the radiation emitted by the material 32 which is then analysed by the CCD controller. The resultant emission spectrum, generally representative of the illuminated material's luminescence characteristics (e.g. peak emission wavelengths, peak intensities, luminescence band intensities, emission spectrum profile), forms the tag of the material being analysed.

In the present context, the tag of a legitimate or authentic material, that is a material whose tag was previously coded in accordance with the imaging techniques described hereinabove for the purpose of subsequent authentication or identification, defines an emission spectrum that is generally represented by at least two luminescence bands having respective emission intensity profiles, each one of which generally defining a main emission peak at a predetermined wavelength (as in A and D of FIG. 1). As such, a given tag, identifying a number of luminescent wavelengths, bands or peaks, each having respective measurable emission intensities, may be provided to the CPU 12 for further processing (e.g. authentication, identification, etc.).

For instance, the CPU 12 may compare, using various software algorithms stored in RAM 16 and/or ROM 14, the emission spectrum of the tag (e.g. wavelengths, intensities, luminescence bands, profile, etc.) with reference data, tags or spectra stored in RAM 16 or ROM 14. For example, if the wavelengths and corresponding peak heights of the wavelengths are approximately the same (i.e. the fluorescing article matches a particular reference tag or spectrum to within a predetermined range) then they are considered to be the same. The CPU 12 can then indicate to the user, for example using the GUI 44, that the fluorescing article matches (or does not match) one of the references or templates lodged in memory. The indication provided to the user via the GUI 44 could be, for example, a visual symbolic indicator, a text message indicator, an audible tone indicator or a light indicator indicating that the fluorescing article has passed or failed the test. Alternatively, raw or processed tag analysis data, generally identifying the wavelengths/intensities determined by the apparatus 10, could be displayed via GUI 44 for manual comparison from an indexed chart or reference data provided for that purpose.

Are person of skill in the art will understand that the reference data, tags or spectra described hereinabove generally consist of data representative of one or more predetermined luminescence characteristics of the coded tags. Such characteristics may be established either prior to coding the respective tags or established from luminescence characteristics previously coded within the respective tags. As stated above, this data may comprise a number of luminescence characteristics such as, but not limited to, peak luminescence wavelengths and intensities, luminescence band characteristics (bandwidth, intensity profile, total integrated intensity, etc.), emission spectra profiles and the like. As such, the term reference tag and/or spectrum is generally meant to define reference data representative of individual or a given set or coded tags for use in authenticating these coded tags, verifying the authenticity of an object with which they are respectively associated, and rejecting tags that do not exhibit these characteristics. Alternatively, physical reference tags exhibiting these luminescent characteristics may also be distributed to various tag identification, verification or monitoring stations for direct comparison with luminescent tags verified thereat.

A person of skill in the art will also understand that a number of numerical, algebraic and/or graphical techniques and algorithms may be considered to compare the emission spectrum of a given tag with one or more reference tag/spectrum. For instance, the above example compares the peak emission intensities of a given tag with the predetermined peak emission intensities provided by one or more reference tags. Alternatively, one could consider the overall emission intensity measured from the tag within at least two detected luminescence bands and compare those intensities with the predetermined band intensities of the one or more reference tags. Comparisons of peak emission intensity ratios, peak emission wavelengths, luminescence bandwidths, integrated spectrum intensities, spectrum profiles and the like may also be considered without departing from the general scope and nature of the present disclosure. Also, as presented hereinabove, tags may be coded using luminescent compositions providing luminescence in more than two luminescence bands and comprising a plurality of peak emission wavelengths. Such tags may thus be coded using a more elaborate scheme of relative intensity ratios and luminescence band comparisons.

Figure 5:
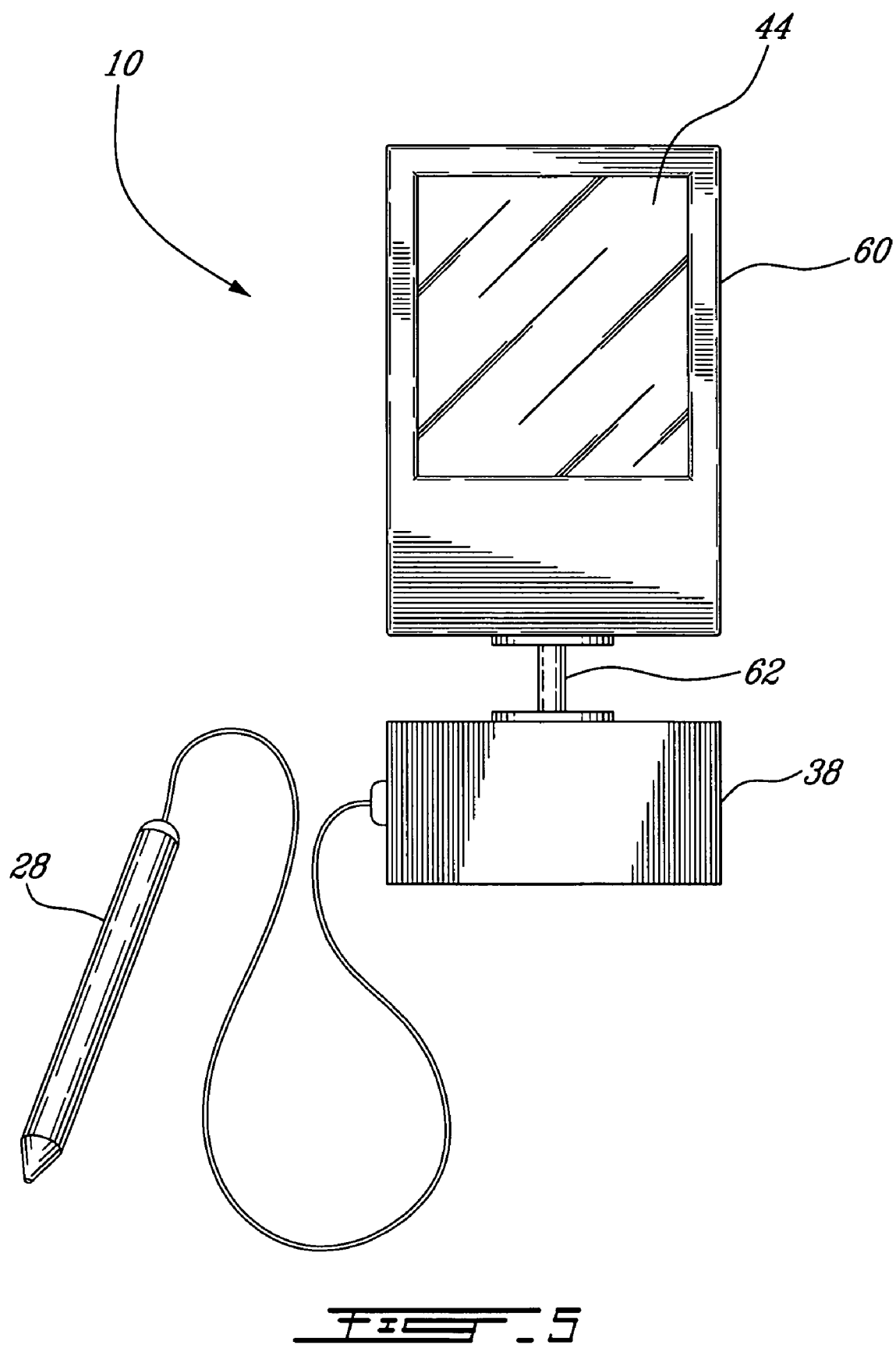
FIG. 5 shows a top plan view of an alternative apparatus for reading FRET encoded tags in accordance with the illustrative embodiment of FIG. 3.

Referring now to FIG. 5, note that the apparatus for reading materials encoded with a luminescent tag 10 could also be implemented in a manner such that the spectrometer 38 and the attached probe 28 are external to the unit 60 which processes the resultant wavelength/intensity tags as determined by the spectrometer 38. In this regard, the unit 60 could be comprised of a small hand held PDA, notebook or desktop computer or the like, with a GUI 44 and suitable software for processing the received wavelength/intensity tags and controlling the spectrometer 38. The unit 60 would be interconnected with the spectrometer 38 for exchanging commands and transferring the detected wavelength/intensity tags using a suitable interface 62 such as a USB interface or the like.

As discussed hereinabove, luminescent compositions as described herein are particularly useful for marking objects with tags which are normally invisible to the naked eye and difficult to replicate. In particular, items on which government duties are levied (such as cigarettes), are often counterfeited (such as luxury designer goods) or monetary instruments (such as paper money) provide prime examples of articles which can be tagged with these luminescent compositions as a method of indicating that the duties have been paid or that the article in question is not counterfeit. As a result, articles which have not been tagged, or are tagged with an incorrect tag, can be quickly recognised and contraband or counterfeit articles readily identified. By equipping customs personnel, for example, with the apparatus of the present invention, identification of contraband or counterfeit articles can take place at points of entry into a particular country. Alternatively, by providing merchants with the apparatus of the present invention contraband or counterfeit articles can be identified at the point of sale.

Figure 10:
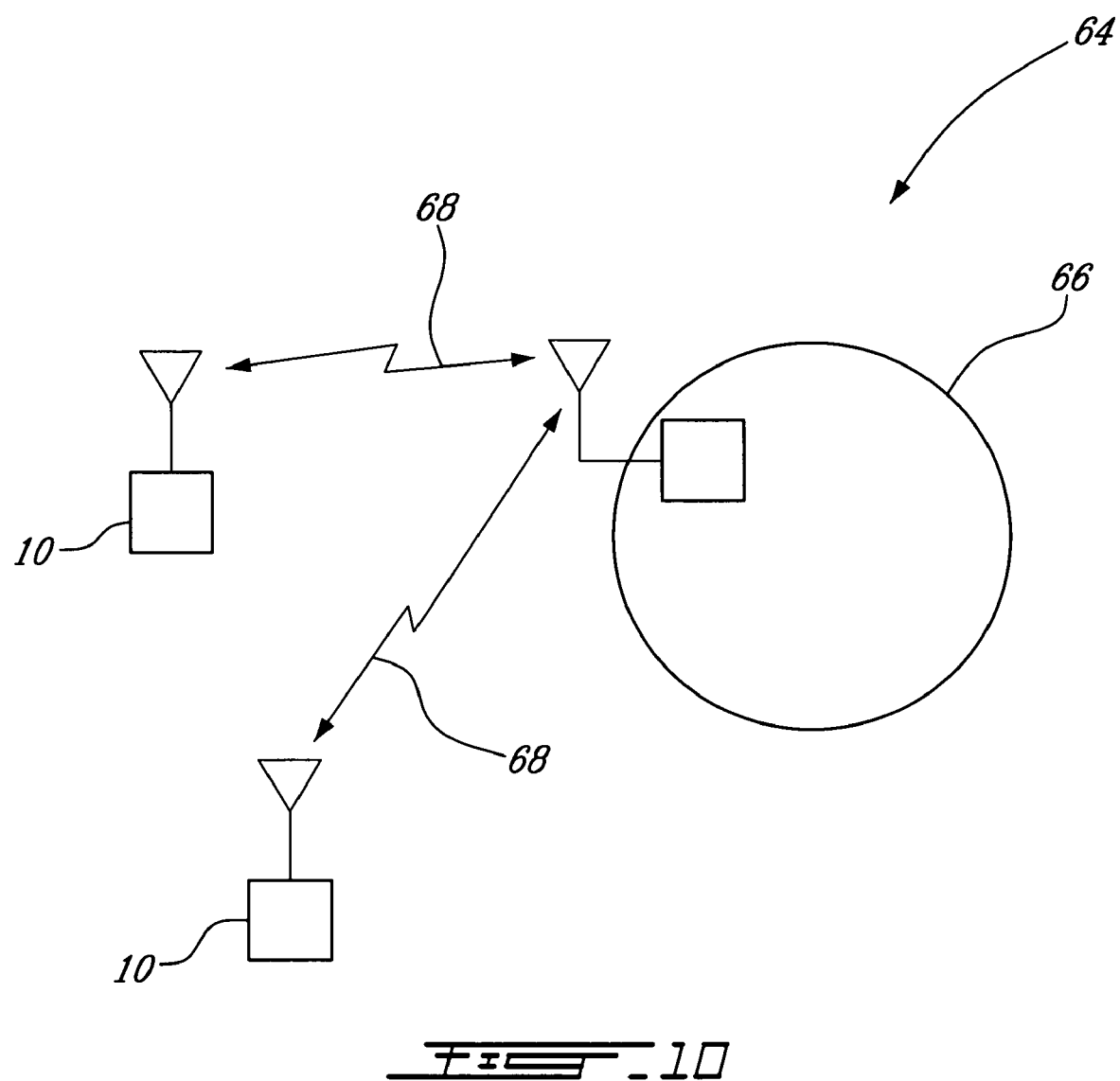
FIG. 10 shows a schematic diagram of a contraband/counterfeit identification and location system integrating the system of FIG. 3.

Referring now to FIG. 10, by integrating the apparatus 10 of the present invention into a system 64 for verifying or monitoring the authenticity of objects, for example via the wireless interface (reference 46 on FIG. 3), a system aimed at identifying, verifying, monitoring and controlling distributed, delivered and sold objects can be realised. For instance, system 64 could be used to verify the authenticity of a plurality of specific objects individually, the authenticity of various object types, classes and qualities, the authenticity of an object's origine, and the like. Namely, such a system 64 could be used as an object contraband/counterfeit identification and location system, an object quality assurance and verification system, or other such systems.

In the illustrative example of a contraband/counterfeit identification and location system, the system 64 could be comprised of a plurality of apparatuses for reading materials encoded with a luminescent tag as in 10 issued to, for example, customs personnel, officers of government agencies, merchants or the like. The apparatuses as in 10 would communicate with a central office or monitoring station 66, and optionally with other remote monitoring stations as in 10 via, for example, a wireless connection 68.

As discussed hereinabove, the wireless connection 68 could be used to remotely reprogram the apparatus 10, for example by downloading new reference tags/spectra to the apparatus 10. Additionally, the wireless connection 68 can be used to upload information concerning the presence or absence of luminescent tags of articles being scanned using the apparatus 10 and whether or not the scanned tags, if present, correspond to one or more templates/reference tag held in memory. Additionally, in certain cases the scanned tags themselves, in either raw or parameterised form, can be uploaded to the central office 66 for further analysis. In particular, scanned objects or materials who either do not comprise a luminescent tag or comprise a luminescent tag that does not correspond with any of the reference tags stored in memory may be flagged to the central office and/or remote stations for future identification or tracking.

Furthermore, by providing each apparatus 10 with a GPS receiver (reference 48 on FIG. 3), the current position of the apparatus 10 at the time a flag is generated can also be uploaded to the central office 66. Such positional information may be used to map flagged events for the purpose of tracking or following counterfeit, unauthenticated or illegitimate objects, for example, as they travel across a given region. Such mappings may also help pinpoint regions seeing a greater influx of illegitimate objects, namely at border crossings and the like.

EXAMPLE 1

Figure 6:
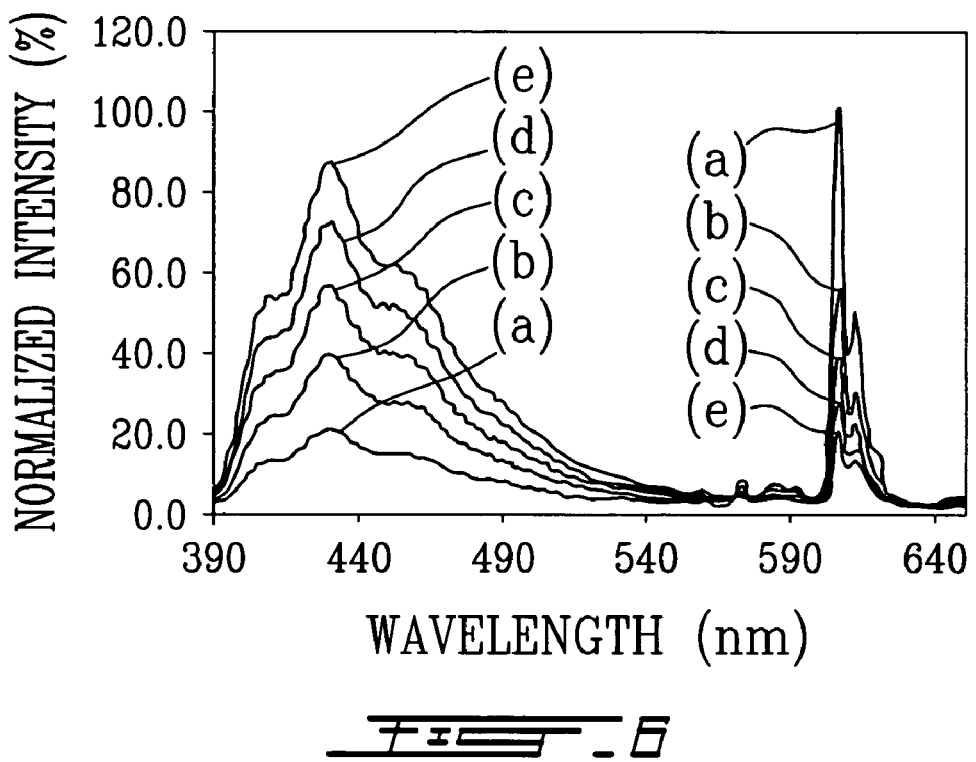
FIG. 6 shows the luminescent spectra of the luminescent composition containing tris(dibenzoylmethane)mono(phenanthroline)europium (III), UVITEX OB and poly(m-ethylmethacrylate) which was coated on polyester film and imaged with a triple Nd:YAG laser at (a) 0 mJ/cm$^2$, (b) 57.0 mJ/cm$^2$, (c) 95.0 mJ/cm$^2$, (d) 142.5 mJ/cm$^2$, and (e) 190.0 mJ/cm$^2$.

Referring now to FIG. 6, five hundred milligrams of tris (dibenzoylmethane)mono-(phenanthroline)-europium (III) (ADS051RE, available from American Dye Source, Inc.) and six hundred milligrams of Uvitex OB (available from Ciba Specialty Chemicals) were dissolved in 200 ml toluene solution containing 20 grams poly(methylmethacrylate) (Molecular weight 120,000, available from Sigma Aldrich). The solution was coated on Mylar film using a wire-wound bar. Uniform colourless film was obtained after drying with hot air gun. When excited with ultraviolet light ($\lambda=370$ nm), the film emits a bright red colour light and the photoluminescent spectrum shows two emission peaks at $\lambda=430$ nm and $\lambda=612$ nm. The former photoluminescent emission peak is the fluorescent characteristic of Uvitex OB, while the later is the fluorescent peak of ADS051RE, respectively.

Figure 7:
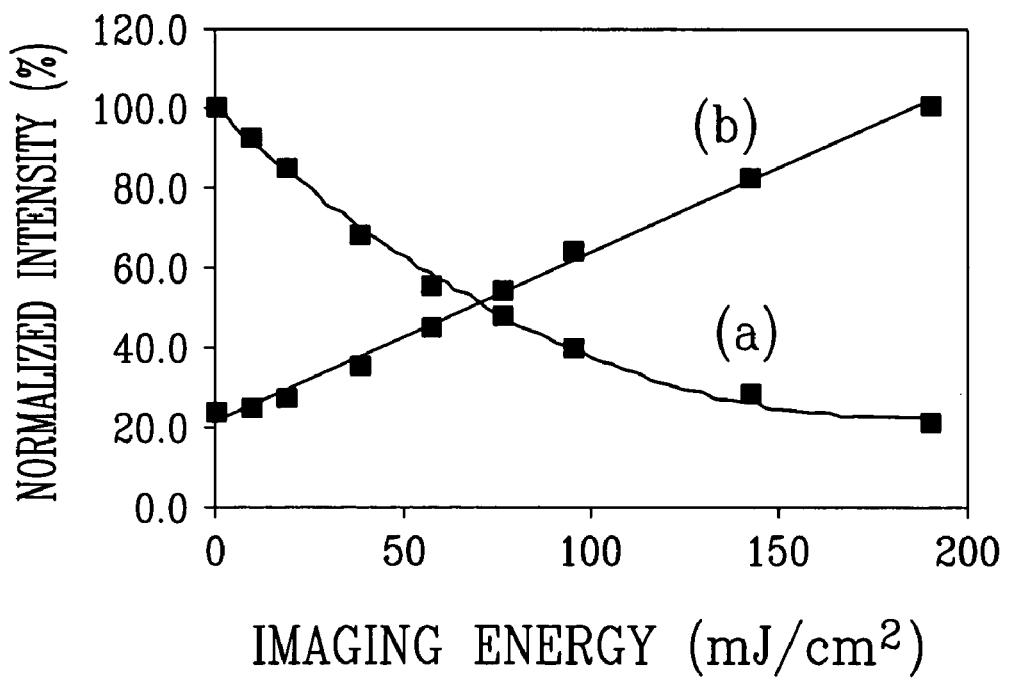
FIG. 7 shows the changes in the intensity of the luminescent peaks of (a) tris(dibenzoylmethane)mono(phenanthroline)-europium (III) at ?=612 nm, and (b) of UVITEX OB at ?=432 nm.

The film was exposed to a high power triple Nd-YAG laser ($\lambda=355$ nm) at different energy densities. No visual colour change was observed with the naked eyes. However, when excited with UV light with a wavelength of $\lambda=370$ nm, the photoluminescent colour of the imaged area changes gradually from red to blue. FIG. 6 shows the photoluminescent spectra of the image area with different laser imaging energy densities. FIG. 7 shows the changes in the intensity of the photoluminescent peaks at $\lambda=430$ nm and $\lambda=612$ nm, respectively, upon increasing laser imaging densities applied to the film.

This example of a combination between Uvitex and europium complex shows a drastic decrease of the intensity of the europium complex fluorescence peak upon exposure to increasing laser imaging doses [(b) 57.0 mJ/cm$^2$, (c) 95.0 mJ/cm$^2$, (d) 142.5 mJ/cm$^2$, and (e) 190.0 mJ/cm$^2$)]. Indeed, it loses up to 80% of its intensity at a laser imaging density of 190.0 mJ/cm$^2$, as compared to only 40% when europium complex is alone in solution, whereas Uvitex fluorescence peak intensity nearly recovers its highest level. This is an indication of the rapid degradation of the europium complex that is thus no more capable of absorbing energy from Uvitex. Therefore, the blue fluorescence of Uvitex re-appears and brightens as the laser imaging density increases.

Also, this example shows that control of the relative intensities of (in this example) red and blue is possible by choosing an appropriate laser imaging density. As shown in FIG. 7, the "shift" point between red and blue for the specific combination of Uvitex and europium is around 70.0 mJ/cm$^2$. This ability to control the relative intensities of the emitted light is used to advantage in the present invention.

It will now be apparent to a person of ordinary skill in the art that the intensities of the wavelengths emitted by the fluorescing material when exposed to UV light with a wavelength of $\lambda=370$ nm will have a relative intensity dependant on the laser imaging density to which the fluorescing material was previously exposed.

EXAMPLE 2

Figure 8:
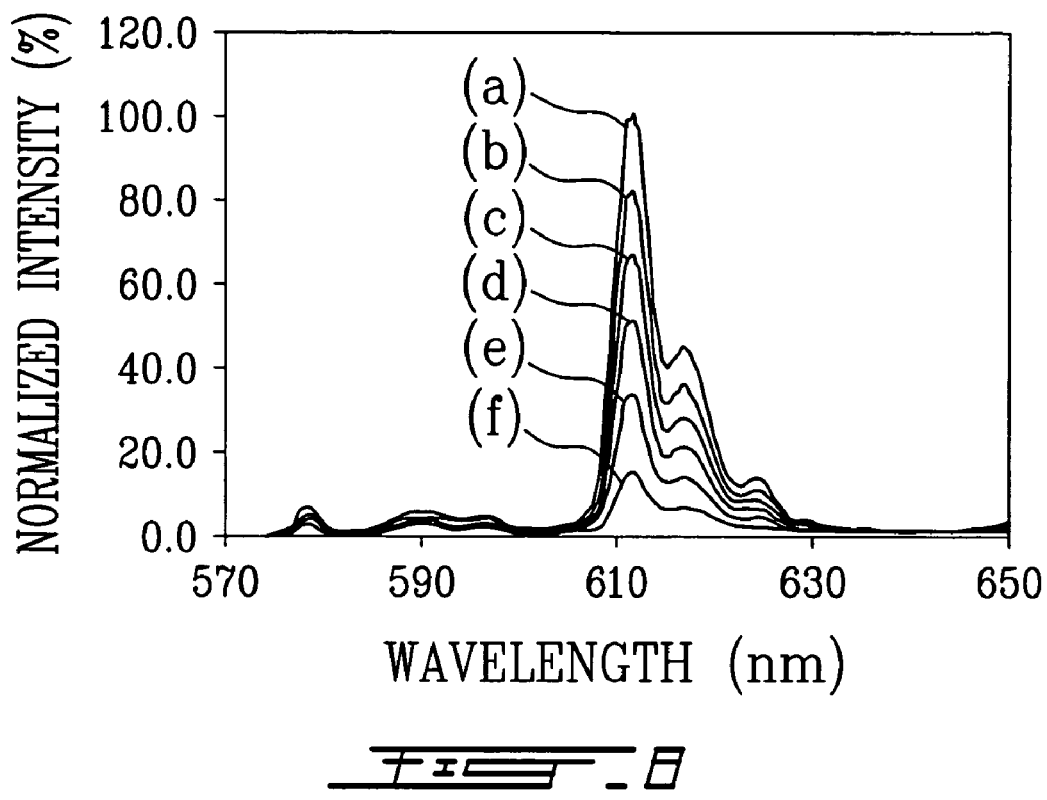
FIG. 8 shows the luminescent spectra of the luminescent composition containing tris(dibenzoylmethane)mono(phenanthroline)europium (III) and polyvinyl carbazole which was coated on polyester film and imaged with a triple Nd:YAG laser at (a) 0 mJ/cm$^2$, (b) 19.0 mJ/cm$^2$, (c) 47.5 mJ/cm$^2$, (d) 95.0 mJ/cm$^2$, (e) 142.5 mJ/cm$^2$ and (f) 190.0 mJ/cm$^2$.
Figure 9:
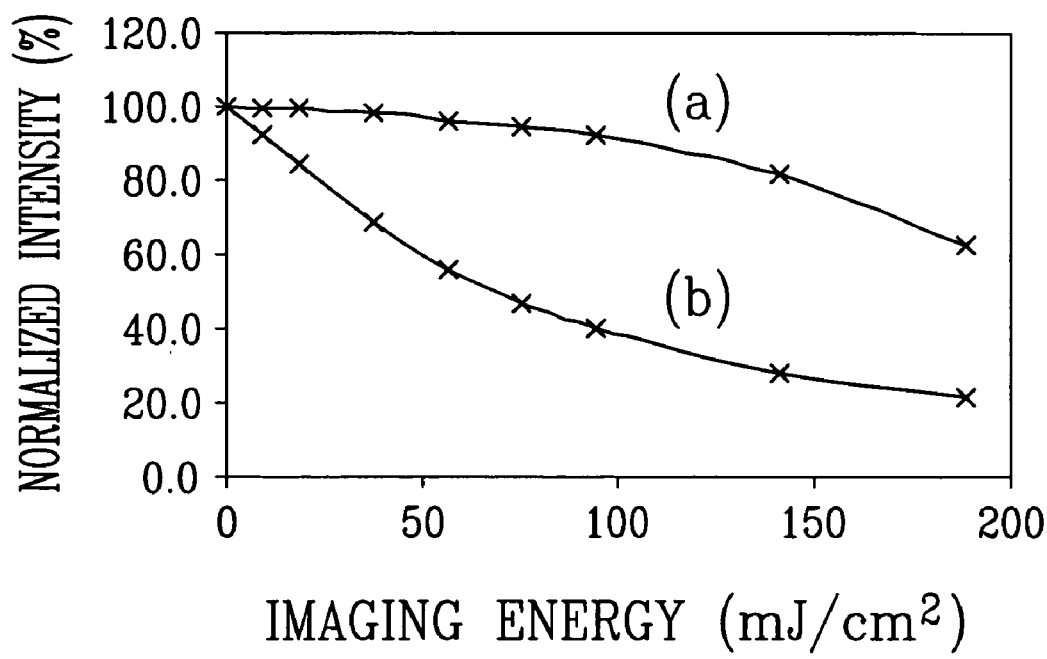
FIG. 9 shows the changes in the intensity of the luminescent peak at ?=612 nm of (a) the luminescent composition containing tris(dibenzoylmethane)mono(phenanthroline)europium (III) and (b) the luminescent composition containing tris(dibenzoylmethane)mono(phenanthroline)europium (III) and polyvinyl carbazole.

Referring to FIG. 8, three hundred milligrams of tris(dibenzoylmethane)mono-(phenanthroline)europium (III) (ADS051RE, available from American Dye Source, Inc.) and seven hundred milligrams of polyvinyl carbazole (Molecular weight 28,000, available from Sigma Aldrich) were dissolved in 200 ml toluene solution. The solution was coated on Mylar film using wire-wound bar. Uniform colourless film was obtained after drying with hot air gun. When excited with ultraviolet light (i.e., ?=370 nm), the film emits a bright red colour light and the luminescent spectrum shows only one luminescent peak at ?=612 nm, which is the fluorescent peak of ADS051RE. This indicated that the fluorescence of polyvinyl carbazole was completely quenched by ADS051RE. The film was then imaged using a triple Nd-YAG laser (?=355 nm) at different energy densities. No visual colour change was observed with the naked eyes. However, upon exposure to deciphering ultraviolet light (i.e., ?=370 nm), the luminescent colour of the film changes gradually from red to colourless with increasing laser energy density. FIG. 8 shows the luminescent spectra of the image area with different laser imaging doses. FIG. 9 shows the changes on the luminescent intensity at ?=612 nm versus the laser imaging energy density.

The presence of polyvinyl carbazole in the luminescent compositions greatly increases the laser imaging speed. Indeed, europium alone loses 40% intensity in its fluorescence peak when the laser imaging energy density is at 190 $mJ/cm_2^2$, whereas it reaches the same level with only 50 $mJ/cm^2$ when in presence of polyvinyl carbazole.

Although the present invention has been described hereinabove by way of illustrative embodiments thereof, these embodiments can be modified at will without departing from the spirit and nature of the subject invention.

What is claimed is:

1. A method for coding a luminescent tag comprising a composition of at least two luminescent compounds, each one of which luminescing within at least one luminescence band, said luminescent compounds comprising at least one donor compound and at least one acceptor compound, an emission spectrum of said donor compound overlapping with an absorption spectrum of said acceptor compound, the method comprising steps of:
   providing a reference tag representative of reference relative light intensities emitted within at least two luminescence bands;
   initially irradiating said luminescent tag with a low power source of electromagnetic radiation such that said luminescent tag emits initial relative light intensities; and
   coding said luminescent tag by irradiating said luminescent tag with a high power source of electromagnetic radiation and adjusting an energy of said high power source of electromagnetic radiation such that when said luminescent tag is subsequently irradiated with a subsequent low power source of electromagnetic radiation measured relative light intensities emitted by the luminescent tag are modified with respect to the initial relative light intensities to match said reference relative light intensities of said reference tag, said high power source of electromagnetic radiation comprising a wavelength which lies within an absorption spectrum of said donor compound.

2. The method of claim 1, wherein said reference tag comprises
   a reference ratio of said reference intensities and wherein said coding step comprises adjusting the energy of said high power source of electromagnetic radiation according to a ratio of said measured intensities subsequently emitted by the luminescent tag so as to match said reference ratio of said reference intensities.

3. The method of claim 1, wherein said reference intensities and
   said measured intensities respectively comprise reference and measured peak emission intensities within said at least two luminescence bands of said reference tag.

4. The method of claim 3, wherein said reference tag comprises
   a representative wavelength for each of said reference peak intensities.

5. The method of claim 1, wherein said low power source of electromagnetic radiation is a source of UV radiation.

6. The method of claim 1, wherein said at least two luminescence bands comprise at least one of a UV band and an IR band.

7. The method of claim 1, wherein said reference tag is representative of reference relative light intensities emitted in plural luminescence bands.

8. The method of claim 1, wherein said providing step comprises providing plural reference tags each representative of respective reference relative light intensities and wherein said coding step includes adjusting the energy of said high power source of electromagnetic radiation according to measured intensities subsequently emitted by the luminescent tag to match any of said respective reference relative light intensities.

9. A method for verifying the authenticity of an object, the method comprising steps of:
   associating a luminescent tag with the object, said luminescent tag comprising a composition of at least two luminescent compounds, each one of which luminescing within one luminescence band, said luminescent compounds comprising at least one donor compound and at least one acceptor compound, an emission spectrum of said donor compound overlapping with an absorption spectrum of said acceptor compound, said luminescent tag being initially irradiated with a low power source of electromagnetic radiation such that said luminescent tag emits initial relative light intensities;
   coding said luminescent tag by irradiating said luminescent tag with a high power source of electromagnetic radiation and adjusting an energy of said high power source of electromagnetic radiation such that when said luminescent tag is subsequently irradiated with a subsequent low power source of electromagnetic radiation adjusted relative light intensities emitted by the luminescent tag are modified with respect to the initial relative light intensities to match reference light intensities within said at least two luminescence bands; and
   authenticating the object by triggering said luminescent tag, measuring a light spectrum emitted thereby and comparing said measured spectrum with a reference spectrum;
   wherein if said measured spectrum matches said reference spectrum, the object is authenticated.

10. The method of claim 9, wherein said coding step further comprises retaining a spectrum of said adjusted light intensities as said reference spectrum.

11. The method of claim 9, wherein said reference spectrum is predetermined and wherein said coding step further comprises adjusting said adjusted relative light intensities to match said reference spectrum.

12. The method of claim 9, the method further comprising the step of generating a reference tag representative of said reference spectrum, said reference tag identifying said adjusted intensities, wherein said light spectrum measuring step comprises measuring light intensities emitted within said luminescence bands by said triggered tag and wherein said comparing step comprises comparing said measured intensities with said adjusted intensities, and further wherein if said measured intensities match said adjusted intensities, the object is authenticated.

13. The method of claim 9, the method further comprising the step of generating a reference tag representative of said reference spectrum, said reference tag identifying a reference ratio of said adjusted intensities, wherein said light spectrum measuring step comprises measuring light intensities emitted within said luminescence bands by said triggered tag and calculating a ratio thereof and wherein said comparing step comprises comparing said calculated ratio with said reference ratio, and further wherein if said calculated ratio matches said reference ratio, the object is authenticated.

14. The method of claim 9, wherein said luminescent tag is coded to identify at least one of a specific object authenticity, an object quality authenticity, an object origin authenticity and an object type authenticity.

15. The method of claim 9, wherein said comparing step comprises comparing said measured spectrum with plural reference spectra and wherein the object is authenticated if said measured spectrum matches any of said reference spectra.

16. The method of claim 9, wherein said authenticating step is performed at a remote monitoring location, said remote monitoring location being provided access to said reference spectrum from at least one of a central monitoring location and a remote monitoring location via a communication network.

17. The method of claim 9, wherein said donor compound and said acceptor compound fluoresce in the UV band.

18. The method of claim 9, wherein said donor compound fluoresces in the UV band and said acceptor compound fluoresces in the infra-red band.

19. The method of claim 9, wherein said associating step comprises printing said compounds on a material comprised in at least one of the object, a wrapper of the object and a container of the object.

20. The method of claim 9, wherein said associating step comprises suspending said compounds in a material comprised in at least one of the object, a wrapper of the object and a container of the object.

21. The method of claim 9, the method further comprising after said authenticating step, communicating a flag to at least one of a central monitoring station and a remote monitoring station when said measured spectrum does not match said reference spectrum.

22. The method of claim 21, said communicating step further comprising communicating a location from which said flag is communicated.

23. The method of claim 9, the method further comprising the step after said authenticating step of indicating whether the object is authenticated via an indicator selected from the group consisting of a symbolic visual indicator, a text indicator, a light indicator and an audio indicator.

24. A system for verifying the authenticity of an object, the system comprising:
a luminescent tag to be associated with the object, said luminescent tag comprising a composition of at least two luminescent compounds, each one of which luminescing within at least one of luminescence band, said luminescent compounds comprising at least one donor compound and at least one acceptor compound, an emission spectrum of said donor compound overlapping with an absorption spectrum of said acceptor compound, said luminescent tag being initially irradiated with a low power source of electromagnetic radiation such that said luminescent tag emits initial relative light intensities, said luminescent tag being coded by irradiating said composition with a high power source of electromagnetic radiation, said high power source of electromagnetic radiation comprising a wavelength which lies within an absorption spectrum of said donor compound, an energy of said high power source of electromagnetic radiation being adjusted such that when said composition is subsequently irradiated with a subsequent low power source of electromagnetic radiation then said luminescent tag emits light within at least two luminescence bands at predetermined relative light intensities that are modified with respect to the initial relative light intensities;
a reference tag representative of said predetermined intensities; and
a monitoring station having access to said reference tag, said station comprising a spectrometer, a data processor and an output device and being configured to measure light intensities emitted within said luminescence bands by said coded tag via said spectrometer, compare said measured intensities with said predetermined intensities and indicate via said output device whether said measured intensities match said predetermined intensities.

25. The system of claim 24, wherein said reference tag comprises a reference ratio of said predetermined intensities, said monitoring station being adapted to calculate a ratio of said measured intensities and compare said calculated ratio with said reference ratio.

26. The system of claim 24, wherein said coded tag is coded to identify at least one of a specific object authenticity, an object quality authenticity, an object origin authenticity and an object type authenticity.

27. The system of claim 24, said monitoring station having access to plural reference tags each representative of respective predetermined light intensities and being configured to indicate whether said measured intensities match any of said respective predetermined light intensities.

28. The system of claim 24, the system further comprising a central station, said monitoring station further comprising a communication device for communicating with said central station, said monitoring station being provided access to said reference tag from said central station via said communication device.

29. The system of claim 24, the system further comprising a central station, said monitoring station further comprising a communication device for communicating a flag thereto when said measured intensities do not match said predetermined intensities.

30. The system of claim 29, said monitoring station further comprising a positioning device for communicating to said central station a location from which said flag is communicated.

31. The system of claim 30, wherein said location is used to produce a mapping of flagged unauthenticated objects.

32. The system of claim 24, wherein said monitoring station comprises the source of low power radiation for illuminating and thereby triggering said coded tag.

33. The system of claim 32, wherein said radiation comprises UV radiation.

34. The system of claim 24, wherein said luminescence bands comprise at least one of a UV band and an IR band.

35. A method for incorporating a luminescent code into a material comprising steps of:
- combining a donor luminescent substance with an acceptor luminescent substance, wherein an emission spectrum of said donor substance overlaps with an absorption spectrum of said acceptor substance;
- initially irradiating said combined substances with a low power source of electromagnetic radiation such that said combined substances emit initial relative light intensities;
- irradiating said combined substances with a high power source of ultraviolet radiation, said high power source of ultraviolet radiation comprising a wavelength which lies within an absorption spectrum of said donor substance;
- adjusting an energy of said high power source of ultraviolet radiation to code said combined substances such that when said combined substances are subsequently irradiated with a subsequent low power source of ultraviolet radiation, an intensity of measurable emissions of said donor substance versus an intensity of peak measurable emissions of said acceptor substance is of a predetermined ratio; and
- combining said combined substances with said material.

36. The method of claim 35, wherein said donor luminescent substance and said acceptor luminescent substance fluoresce in the UV band.

37. The method of claim 35, wherein said donor luminescent substance fluoresces in the UV band and said acceptor luminescent substance fluoresces in the infra-red band.

38. The method of claim 35, wherein said combining step comprises printing said combined substances onto said material.

39. The method of claim 35, wherein said combining step comprises suspending said combined substances in said material.

40. The method of claim 35, wherein said combining step is carried out prior to said irradiating and adjusting steps.

* * * * *